United States Patent [19]
Bertness

[11] Patent Number: 6,121,051
[45] Date of Patent: Sep. 19, 2000

[54] FRACTIONAL PHASE MEASUREMENT BY POLARIZATION-DEPENDENT SPECTROSCOPY

[75] Inventor: Kristine A. Bertness, Boulder, Colo.

[73] Assignee: The United States of America as represented by the Secretary of Commerce, Washington, D.C.

[21] Appl. No.: 09/003,727

[22] Filed: Jan. 7, 1998

Related U.S. Application Data

[60] Provisional application No. 60/038,239, Feb. 19, 1997.

[51] Int. Cl.$^7$ .................................................. G01J 3/447
[52] U.S. Cl. ........................ 436/164; 436/55; 117/85; 117/86; 356/327; 356/364
[58] Field of Search ...................... 436/55, 164; 356/322, 356/327, 364–370, 301–304; 117/85, 86, 952

[56] References Cited

U.S. PATENT DOCUMENTS

| | | |
|---|---|---|
| 3,941,482 | 3/1976 | Schneider . |
| 4,434,025 | 2/1984 | Robillard . |
| 4,931,132 | 6/1990 | Aspnes et al. . |
| 5,365,067 | 11/1994 | Cole et al. . |
| 5,552,327 | 9/1996 | Bachmann et al. . |
| 5,582,646 | 12/1996 | Woollam et al. . |
| 5,739,909 | 4/1998 | Blayo et al. . |

OTHER PUBLICATIONS

Azzam et al., J. Opt. (Paris), vol. 12, pp. 317–321, 1981.
Abernathy, C.R. et al. (1995), "Electrical and structural properties of $In_xGa_{1-x}N$ on GaAs," Appl. Phys. Lett. 66(13):1632–1634.
Luo, J.S. et al. (1994), "Investigation of spontaneous ordering in GaInP using reflectance difference spectroscopy," J. Vac. Sci. Technol. B 12(4):2552–2557.
Miyoshi, S. et al. (1992), "MOVPE growth of cubic GaN on GaAs using dimethylhydrazine," J. Cryst. Growth 126:439–442.
Okumura, H. et al. (1991), "Epitaxial growth of cubic and hexagonal GaN on GaAs by gas–source molecular–beam epitaxy," Appl. Phys. Lett. 59(9):1058–1060.
Aspnes, D.E. et al. (1988), "Application of reflectance difference spectroscopy to molecular–beam epitaxy of GaAs and AlAs," J. Vac. Sci. Technol. A6:(3):1327–1332.
Yu, G. et al. (1997), "Polarized Reflectance Spectroscopy and Spectroscopic Ellipsometry Determination," Jpn. J. Appl. Phys. 36(8A):L1029–L1031.
Dietz, N. et al. (1996), "Real–time optical monitoring of $Ga_xIn_{1-x}P$ and GaP heteroepitaxy on Si under pulsed chemical beam conditions," J. Cryst. Growth 164:34–39.

*Primary Examiner*—Jan Ludlow
*Attorney, Agent, or Firm*—Greenlee Winner & Sullivan

[57] ABSTRACT

This invention provides an inexpensive, noninvasive optical method of quantitatively determining the volume fraction of anisotropic material in a mixture of anisotropic and isotropic material, and more particularly for determining the volume fraction of noncubic crystalline material in a mixed-phase specimen having noncubic crystalline material intermixed with cubic crystalline material. Polarized light is impinged on the specimen and the reflectance or transmission difference between two orthogonal polarization directions is measured. In cubic regions the reflectance or transmission is the same along both polarization directions so the contributions to the difference cancel, leaving a signal only from the noncubic regions. The optical difference can be measured as a function of wavelength and critical points in the band structure, including the band gap, can be profiled. From the band structure the film composition can be determined. This measurement is particularly suited to measuring III–V nitride semiconductor specimens having regions with zincblende symmetry mixed with regions of wurtzite symmetry.

20 Claims, 2 Drawing Sheets

FRACTIONAL PHASE MEASUREMENT BY POLARIZATION-DEPENDENT SPECTROSCOPY

This application claims benefit of Provisional Application Serial No. 60/038,239 filed Feb. 19, 1997.

BACKGROUND OF THE INVENTION

The crystal structure and the band gap are important characterizations of semiconductor materials, both during and after growth. Crystal structure determination is particularly important for materials that can grow in more than one crystal form or in a mixed phase material. For example, although most III–V semiconductors, such as GaAs and InP, grow in the zincblende crystal structure with cubic symmetry, the III–V nitrides are important exceptions. For GaN, AlN, InN and alloys between these compounds the lowest energy configuration is in the wurtzite or hexagonal crystal structure. When these nitrides are grown on a substrate of a different material, the resulting film can be a mixture of wurtzite and zincblende regions. In production of III–V nitride devices such as LEDs, transistors and lasers, characterization of the crystal structure is required.

X-ray analysis can be used to determine the relative amounts of different crystal structures in a mixed-phase specimen (Abernathy et al., Appl. Phys. Lett. 66, 1995, p. 1632). However an x-ray system is expensive and cannot readily be used during crystal growth. Reflection high energy electron diffraction (RHEED) can be used to determine the crystal phase during crystal growth (Okumura et al., Appl. Phys. Lett. 59, 1991, p. 1058). However, RHEED is difficult to quantify in terms of volume fraction and neither RHEED nor x-ray analysis gives band gap information. RHEED is also limited to growth techniques taking place under vacuum conditions.

Reflectance difference spectroscopy (RDS) has been used to study the surface structure of purely zincblende III–V semiconductors during crystal growth (Aspnes et al., J. Vac. Sci. Technol. A 6, 1988, p. 1327). The cancellation of the bulk signal due to the crystal symmetry makes it possible to measure the much smaller contributions of the surface to the reflectivity. RDS has also been used to study bulk ordering in zincblende alloys (particularly $Ga_{0.52}In_{0.48}P$). With bulk ordering, the crystalline phase remains unchanged but the species rearrange within the layers. The partial bulk ordering breaks the zincblende symmetry of the lattice and thereby produces an RDS signal. Polarized reflectance spectroscopy has also been used to obtain the refractive indices of hexagonal GaN (Yu et al. (1997) Jpn. J. Appl. Phys. 36(8A):L1029).

SUMMARY OF THE INVENTION

This invention provides an inexpensive, noninvasive optical method of quantitatively determining the volume fraction of noncubic crystalline material in a mixed-phase specimen having noncubic crystalline material intermixed with cubic crystalline material. Polarized light is impinged on the specimen and the reflectance or transmission difference between two orthogonal polarization directions is measured. In cubic regions the reflectance or transmission is the same along both polarization directions so the contributions to the difference cancel, leaving a signal only from the noncubic regions. This measurement is particularly suited to measuring III–V nitride semiconductor specimens having regions with zincblende symmetry mixed with regions of wurtzite symmetry.

This invention further includes a method of determining the volume fraction of any anisotropic material in a mixture with any isotropic material, of which noncubic and cubic crystalline materials are an example. Other examples of isotropic materials are amorphous materials and disordered materials, such as randomly aligned polycrystalline material.

The light source can be monochromatic or it can be polychromatic and the analysis can further include a filter to select the wavelength. The filter can be a spectrometer for scanning the wavelength and the optical difference can be measured as a function of wavelength. Because the optical difference is greatest at critical points in the band structure, including the band gap, the band structure can be profiled. From the band structure the film composition can, in cases such as binary and ternary compounds, be determined.

In a preferred embodiment the optical difference is measured using reflectance difference spectroscopy. The input light is linearly polarized and the reflected light is analyzed using a photoelastic modulator in combination with a polarizer.

DETAILED DESCRIPTION OF THE INVENTION

This invention provides a method of determining the volume fraction of anisotropic material in a mixed specimen having anisotropic material intermixed with isotropic material. This invention is described below in terms of the exemplary case of a noncubic crystalline material mixed with cubic crystalline material. The description applies to the general anisotropic/isotropic mixtures as well.

Figure 1:
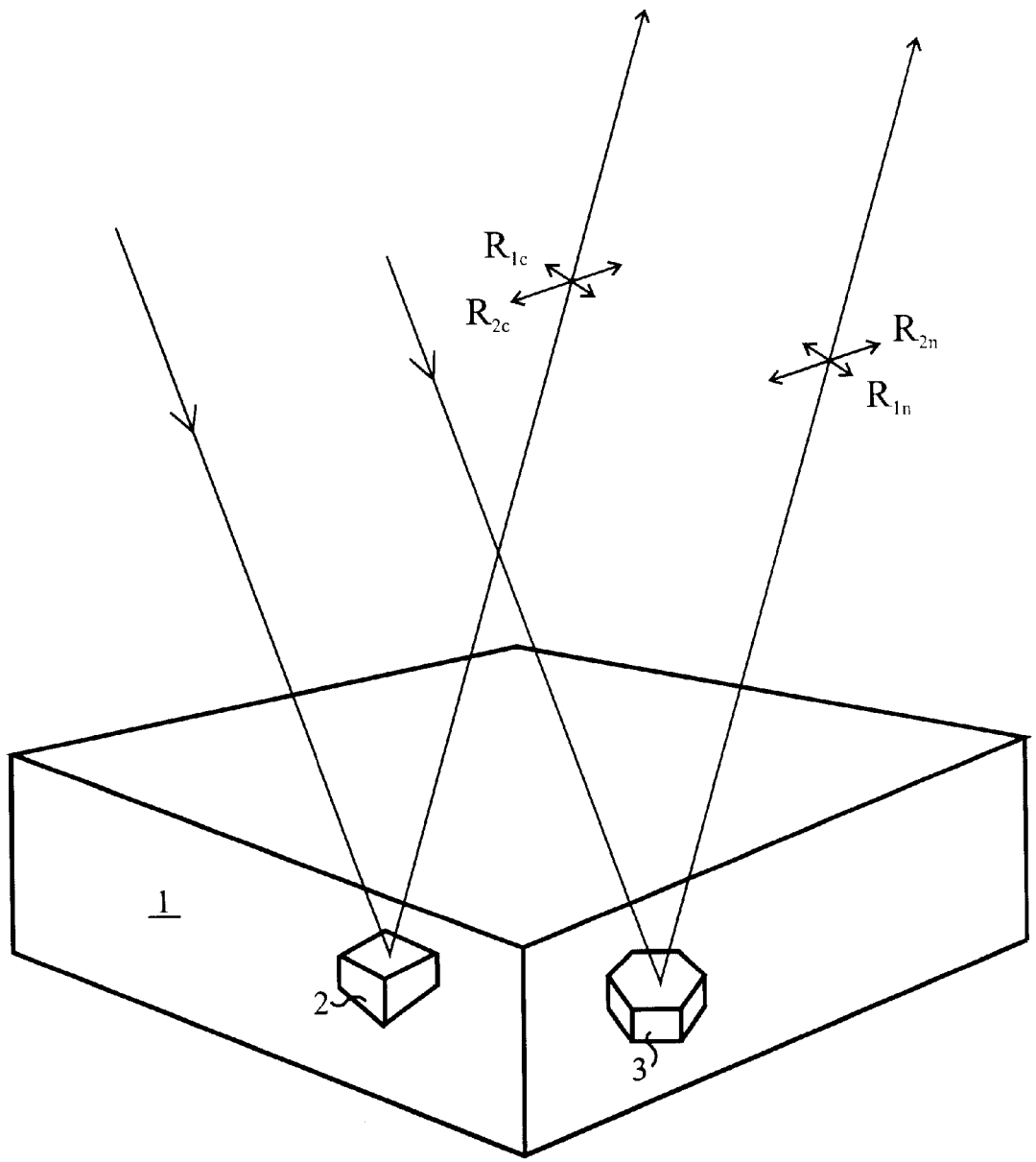
FIG. 1 shows schematically reflection from a specimen having regions of cubic crystal structure and regions of noncubic crystal structure.

As illustrated in FIG. 1, mixed-phase specimen 1 has regions of cubic crystalline material 2 and regions of noncubic crystalline material 3. The two phases generally fill the entire volume of the specimen, with the cubic phase dominating. For conceptual illustration the crystal domains are shown with different macroscopic shapes, though this need not be the actual case. Polarized light is incident on the specimen, preferably oriented at 45° to the crystalline axis of the cubic material so that the light has equal components in both the [110] and [$\bar{1}$10] directions. The light is reflected by both crystalline structures but, for the noncubic material, the reflectance is polarization dependent. Due to the small penetration depth of the incident light, most of the reflection occurs at the surface. For illustration, the magnitudes of the orthogonally polarized components of the reflected light, $R_1$ and $R_2$, are represented by the size of the field direction arrows on the reflected rays. Regions of the specimen with cubic crystalline structure have identical bulk reflectivity in the two polarization directions, so the polarization is unchanged by reflection and $R_{1C}=R_{2C}$. Regions with noncubic crystalline structure have polarization dependent reflectance, so $R_{1n} \neq R_{2n}$. The only contribution to the difference between the two components of the reflectance comes from $R_{1n}-R_{2n}$. The difference between the reflectance components, $\Delta R$, increases with the volume fraction of the noncubic material.

Obtaining the volume fraction from $\Delta R$ requires a conversion step. The intensity of the reflectance depends not only on the volume fraction but also on the optical apparatus and on the reflectivity of the material. To remove the dependence on the measurement system $\Delta R$ can be normalized by dividing by the total reflectance, R. The reflectivity can be calculated theoretically from the material properties, in particular the density of states and matrix elements for the transitions at the signal wavelength. Alternatively a calibration can be performed to correlate the measured reflectance with the volume fraction. The preferred calibration technique is to measure the reflectance of pure samples of each material structure, for example for the III–IV nitrides a pure cubic sample and a pure wurtzite sample. Although $\Delta R$ is not necessarily a linear function of the volume fraction of noncubic material, for most materials the deviation from linearity is expected to be insignificant, especially at low volume fractions. In the case of a nonlinear relationship, intermediate calibration points using mixed phase reference samples can be employed. The measurement can also be calibrated by measuring the volume fraction of some mixed phase specimens by a second technique such as x-ray diffraction. The calibration of one compound can be extended to related compounds using the calculated theoretical differences between the compounds.

The volume fraction measurement has been described in particular for III–V nitrides. It is also useful for other crystalline material, semiconducting, insulating and conducting. For example, in the growth of diamond thin films it can be used to distinguish cubic diamond regions from hexagonal graphite regions.

Cubic crystalline material is one example of an isotropic material. A second example is amorphous material. The appearance of anisotropic crystals within an amorphous film can be monitored. Similarly disordered material at the grain boundaries of polycrystalline material is isotropic. For example, perovskite materials, such as $YBa_2Cu_3O_{7-y}$ and other high critical temperature superconductors, form in hexagonal crystal grains with disordered material at the grain boundaries. Another example is II–VI polycrystalline films, such as CdS and CdTe, which form in the hexagonal wurtzite form. The grains have a polarization dependent reflectance difference, but the signal for the material decreases when there are more grain boundaries or amorphous regions. The volume fraction of the crystalline material can be measured by reflection difference.

If the grains in polycrystalline material are randomly or incompletely aligned, it leads to cancellation of the polarization dependent scattering. Even if the individual grains are anisotropic, the net effect of differently aligned grains is optically isotropic. Thus reflection difference can be used to determine the degree of alignment of the grains within a polycrystalline material. This can be thought of as the volume fraction of aligned (anisotropic) grains. By rotating the sample or the polarization of incident light, the preferred alignment can be identified.

Analogously to polycrystalline material, disorder within a crystal can be monitored. For example, the crystal structure of lithium niobate changes with applied field. The structure remains hexagonal (anisotropic) but the position of the oxygen atoms moves within the lattice. This creates disorder which reduces the anisotrophy. The volume fraction of nondisordered crystal can be measured.

The invention has been described using reflection difference. For anisotropic regions, the transmission is also polarization dependent and can be measured in lieu of the reflectance. The term optical difference is used herein for both reflectance difference and transmission difference. For transmission measurements both the substrate and the specimen must be transparent. Many semiconductor layers are sufficiently transparent near their bandgaps, which is generally the preferred region, for measurement. The bandgap of the substrate is preferably greater than that of the specimen so that it is transparent at the measurement wavelength. Sapphire is a particularly suitable substrate.

Figure 2:
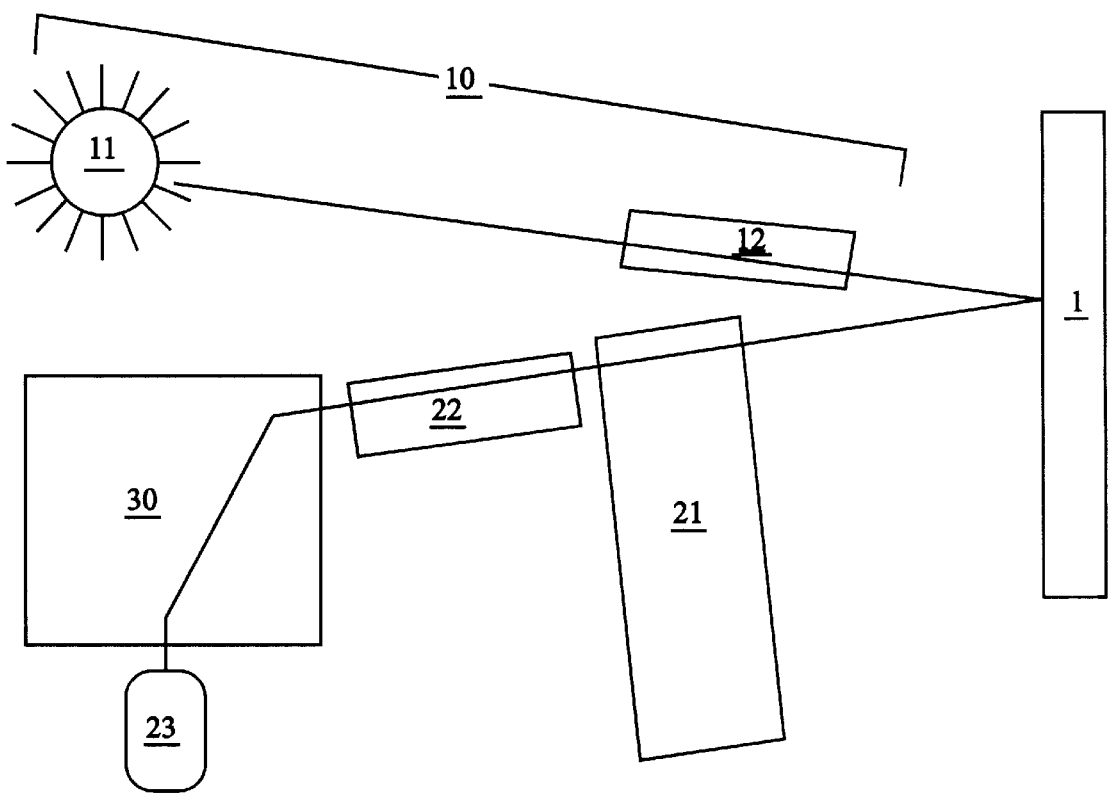
FIG. 2 is a reflectance difference spectroscopy apparatus.

Apparatus for reflectance difference spectroscopy is illustrated in FIG. 2. Polarized light source 10 comprises lamp 11 and polarizer 12. For cubic/noncubic mixed phases, the polarization axis is preferably aligned so that the axis bisects the [110] and [$\bar{1}$10] axes of the cubic material. The light is reflected by mixed-phase specimen 1 to an optical difference measuring apparatus comprising photoelastic modulator 21, analyzing polarizer 22 and photodetector 23. The illustrated embodiment also includes spectrometer 30.

The lamp is selected to provide an output in the wavelength regions of interest for the specimen. For III–V nitrides, in a preferred embodiment the lamp is a Xe arc lamp having an output in the ultraviolet beyond 250 nm. The light source can be monochromatic if band structure information is not required. It can alternatively be a polychromatic source used in combination with a filter. The filter can be a passive filter providing a fixed transmission band, or a tunable filter to enable measurement of the reflectance difference as a function of wavelength. In the illustrated embodiment it is a spectrometer. The filter can be placed after the specimen in the optical path or before the specimen, for example between the lamp and the polarizer.

Optical difference measurement apparatus is described in more detail in Aspnes et al. (J. Vac. Sci. Technol. A 6, 1988, p. 1327), which is incorporated by reference herein in its entirety. In the preferred embodiment, the apparatus includes a photoelastic modulator to sinusoidally vary the polarization as a function of time. The photoelastic modulator is aligned parallel to polarization of incident light. It is followed by an analyzing polarizer oriented at 45° to the incident polarization. The reflected light is detected by a photodetector and the detected signal is processed with a lock-in amplifier synchronized to the photoelastic modulation. The signal is analyzed to obtain the difference in reflectance between orthogonal polarizations, $\Delta R$, and the total reflectance, R.

Control over the light source energy (wavelength) has several advantages. Because the polarization asymmetry varies with the energy, the wavelength can be varied to find the strongest signal. The optimal wavelength can also be chosen to minimize signal from surface effects. By measuring the reflectance difference as a function of wavelength, the critical points in the band structure of the anisotropic material, for example, a noncubic crystalline material, can be measured, and from this the film composition can be determined. Wavelength variation can also be used for the case where there is more than one anisotropic phase in the specimen. If the bandgaps of the two phases are sufficiently separated they can be distinguished by the wavelength dependence of the reflectance.

The measurement can be used interactively to control film growth. For example, in many III–V nitride devices the wurtzite structure is preferred. To obtain the desired structure, deposition parameters such as source evaporation power, cracker temperature, gas flow rates, substrate temperature and chamber pressure can be modified in response to the measured volume fraction. For deposition of alloys, such as alloys of III–V nitrides, the deposition parameters can be coupled to the measured critical points.

Measurement apparatus using a photoelastic modulator has been described. While this is preferred for in situ measurements, for bench top measurements less expensive, if perhaps less sensitive, techniques with a rotating sample and rotating analyzer can be used, as described by Aspnes et al. These and other variations in the measurement technique and in the crystalline material measured will be readily apparent to those skilled in the art and fall within the range and scope of this invention.

I claim:

1. An optical method of determining the volume fraction of anisotropic material in a specimen having anisotropic material intermixed with isotropic material, said method comprising the steps of:

impinging polarized light on the specimen;

measuring the difference in magnitudes of orthogonally polarized components of light reflected from or transmitted by said specimen; and calculating the volume fraction of anisotropic material from said difference.

2. The optical method of claim 1 wherein said difference is the transmission difference.

3. The optical method of claim 1 wherein said difference is the reflectance difference.

4. The optical method of claim 3 wherein said step of measuring the difference utilizes a photoelastic modulator in combination with an analyzing polarizer.

5. The optical method of claim 1 wherein said anisotropic material is noncubic crystalline material and said isotropic material is cubic crystalline material.

6. The optical method of claim 5 wherein the axis of the impinging light is oriented between the [110] and [$\bar{1}$10] directions of said cubic crystalline material.

7. The optical method of claim 5 wherein said specimen is a III–V nitride.

8. The optical method of claim 7 wherein said III–V nitride is selected from the group consisting of GaN, AlN, InN and alloys thereof.

9. The optical method of claim 7 wherein said noncubic crystalline material is a hexagonal structure material.

10. The optical method of claim 1 wherein said isotropic material is an amorphous material.

11. The optical method of claim 1 wherein said specimen is a polycrystalline material.

12. The optical method of claim 11 wherein said isotropic material is at crystal grain boundaries.

13. The optical method of claim 11 wherein said isotropic material is nonaligned crystal grains.

14. The optical method of claim 1 further including the step of wavelength filtering the light before or after impinging on said specimen.

15. The optical method of claim 14 further including the step of scanning the wavelength of said light and measuring the wavelength dependence of said difference.

16. The optical method of claim 15 wherein said anisotropic material is a noncubic crystalline material, further including the step of determining the critical band structure points of said noncubic crystalline material from said wavelength dependence of said difference.

17. The optical method of claim 16 further including the step of determining the composition of said noncubic crystalline material from said critical band structure points.

18. The optical method of claim 16 used during crystal growth of said specimen and further including the step of controlling a deposition parameter in response to said critical structure points.

19. The optical method of claim 1 used during growth of said specimen.

20. The optical method of claim 19 further including the step of controlling a deposition parameter in response to the measured volume fraction.

* * * * *